US00PP21175P2

(12) United States Plant Patent
Smith

(10) Patent No.: US PP21,175 P2
(45) Date of Patent: Jul. 27, 2010

(54) ***CHRYSANTHEMUM* PLANT NAMED 'YOLINDSAY'**

(50) Latin Name: *Chrysanthemum×morifolium*
Varietal Denomination: Yolindsay

(75) Inventor: Mark A. Smith, Fort Myers, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/459,456

(22) Filed: Jul. 1, 2009

(51) Int. Cl.
*A01H 5/00* (2006.01)

(52) U.S. Cl. ..... Plt./287

(58) Field of Classification Search ..... Plt./287, Plt./291

See application file for complete search history.

*Primary Examiner*—June Hwu
(74) *Attorney, Agent, or Firm*—S. Matthew Edwards

(57) ABSTRACT

A new *Chrysanthemum* plant named 'Yolindsay,' particularly distinguished by the greyed-purple decorative type, medium sized flowers; medium green foliage, with medium size upright and mounded habit.

1 Drawing Sheet

Latin name of the genus and species of the plant claimed: *Chrysanthemum×morifolium.*

Varietal denomination: 'Yolindsay'.

BACKGROUND OF THE NEW PLANT

The present invention comprises a new *Chrysanthemum*, botanically known as *Chrysanthemum×morifolium*, and hereinafter referred to by the variety name 'Yolindsay'.

'Yolindsay' is a product of a planned breeding program. The new cultivar has greyed-purple decorative type, medium sized flowers; medium green foliage with medium size upright and mounded habit.

'Yolindsay' originated from a hybridization made in January 2005 in a controlled breeding environment in Salinas, Calif. 'Yolindsay' was selected as one flowering plant within the progeny of the stated cross in the November 2005 in a controlled environment in Alva, Fla.

The female parent was the proprietary plant designated 'Branbeach,' unpatented. 'Branbeach' has more disc flowers; more salmon and less coral colored flowers than 'Yolindsay'.

The male parent of 'Yolindsay' was an unpatented hybrid seedling identified as 'OO-M34' with red colored flowers, non-uniform plant habit, more susceptible to Fusarium; and a natural season response that is one week faster.

The first act of asexual reproduction of 'Yolindsay' was accomplished when vegetative cuttings were propagated from the initial selection in January 2006 in a controlled environment in Alva, Fla.

BRIEF SUMMARY OF INVENTION

Horticultural examination of plants grown from cuttings of the plant initiated in January 2006, and continuing thereafter, has demonstrated that the combination of characteristics as herein disclosed for 'Yolindsay' are firmly fixed and are retained through successive generations of asexual reproduction.

'Yolindsay' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Chrysanthemum* as a new and distinct variety.

Plant Breeder's Rights for this cultivar have not been applied for. 'Yolindsay' has not been made publicly available more than one year prior to the filing of this application.

BRIEF DESCRIPTION OF THE PHOTOGRAPHS

The accompanying photographic drawing shows typical flower and foliage characteristics of 'Yolindsay' with colors being as true as possible with an illustration of this type. The photographic drawing shows a flowering potted plant of the new variety and a close-up of the flowers.

DETAILED BOTANICAL DESCRIPTION

The plant descriptions and measurements were taken in Salinas, Calif. in early June 2009 under natural light. The aforementioned photographs were taken in Gilroy, Calif. in early June 2009. These plants were started and grown in Alva, Fla. and were shipped to California in late May 2009. Plants were grown under conditions which approximate those generally used in commercial potted *Chrysanthemum* production. These plants used in the photograph and descriptions were about 8 to 10 weeks old.

Color references are made to The Royal Horticultural Society Colour Chart (R.H.S.) 2001.

TABLE 1

DIFFERENCES BETWEEN THE NEW VARIETY 'YOLINDSAY' AND A SIMILAR VARIETY

| | 'Yolindsay' | 'Yojenna' (U.S. Plant Pat. No. 17,532) |
|---|---|---|
| Flower size: | Smaller | Larger |
| Flower color: | Closest to RHS 186B | About RHS 58A |
| Plant size: | Larger, round habit | Smaller, less round |
| Natural flowering response: | One week slower | One week faster |
| Susceptibility to Fusarium: | Less susceptible | More susceptible |

Plant:

*Form, growth and habit.*—Herbaceous decorative garden-type. Stems upright and outwardly spreading, freely branching, strong and moderately vigorous growth habit.

*Plant height.*—20-22 cm.

*Plant height* (*inflorescence included*).—22-25 cm.

*Plant width.*—38-43 cm.

*Garden performance and tolerance to weather.*—Good.

*Crop time to flowering.*—About 42-48 days.

Roots:

*Number of days to initiate roots.*—4 days at about 21 degrees C.

*Number of days to produce a rooted cutting.*—10-12 days at 21 degrees C.

*Type.*—Fine, fibrous, free branching.

*Color.*—RHS N155B but whiter.

Foliage:

*Arrangement.*—Alternate, simple.

*Immature, leaf color, upper surface.*—RHS 137A.

*Lower surface.*—RHS 147B.

*Mature, leaf color, upper surface.*—RHS 137A.

*Lower surface.*—RHS 147B.

*Length.*—5.0-5.6 cm.

*Width.*—3.9-4.2 cm.

*Shape.*—Ovate.

*Base shape.*—Attenuate.

*Apex shape.*—Mucronulate.

*Margin.*—Palmately lobed, slightly serrate.

*Texture, upper surface.*—Bifid T-shaped hairs.

*Lower surface.*—Bifid T-shaped hairs.

*Color of veins, upper surface.*—Closest to RHS 147C.

*Color of veins, lower surface.*—Closest to RHS 147C.

*Petiole color.*—RHS 147C.

*Length.*—0.6-0.8 cm.

*Diameter.*—0.3 cm.

*Texture.*—Bifid T-shaped hairs.

Stem:

*Quantity of main branches per plant, after removal of terminal apex* (*pinching*).—10-12.

*Quantity of leaves per branch.*—About 14.

*Color of stem.*—Closest to RHS 146B but appears lighter because of heavy amount of hairs.

*Length of stem.*—12-15 cm.

*Diameter.*—0.5 cm.

*Length of internodes.*—0.6-0.8 cm.

*Texture.*—Bifid T-shaped hairs.

*Color of peduncle.*—Closest to RHS 147B.

*Length of peduncle.*—4.5-5.5 cm.

*Peduncle diameter.*—0.2-0.25 cm.

*Texture.*—Bifid T-shaped hairs.

Inflorescence:

*Type.*—Compositate type, solitary inflorescences (decorative-type) borne terminally above foliage, ray florets arranged acropetally on a capitulum.

*Blooming habit.*—Natural season flowering around mid September.

*Quantity of infloresences per plant.*—About 125.

*Quantity of inflorescences per lateral stem.*—About 9-12 with additional buds.

*Lastingness of individual blooms on the plant.*—3½ weeks.

*Fragrance.*—Slightly spicy.

Bud (just before opening/showing color):

*Color.*—RHS 184C.

Length.—0.7-0.8 cm.

*Width.*—0.7-0.8 cm.

*Shape.*—Oblate.

Immature inflorescence:

*Diameter.*—3.5-4.5 cm.

*Color of ray florets, upper surface.*—Closest to RHS 186A but a little lighter.

*Lower surface.*—Closest to RHS 186A but a little lighter.

Mature inflorescence:

*Diameter.*—4.7-5.5 cm.

*Depth.*—0.5 cm.

*Total diameter of 'disc'.*—0.4-0.6 cm.

*Recepticle height.*—0.5 cm.

*Recepticle diameter.*—0.7-0.8 cm.

Ray florets:

*Average quantity of florets.*—100 in numerous whorls.

*Color of florets, upper surface.*—Closest to RHS 186B but a little lighter.

*Lower surface.*—Closest to RHS 39D.

*Length.*—1.9-2.3 cm.

*Width.*—0.5-0.6 cm.

*Shape.*—Oblong.

*Apex shape.*—Praemorse.

*Margin.*—Entire.

*Texture, upper surface.*—Papillose.

*Lower surface.*—Papillose.

Disc flowers:

*Average quantity of florets.*—About 25-35.

*Color of florets.*—RHS 155C basally and RHS 6A at the apex.

*Length.*—0.4 cm.

*Width.*—0.1 cm.

*Shape.*—Tubular.

*Apex shape.*—Acute, 5 pointed.

Phyllaries:

*Quantity.*—Approximately 50-100.

*Color, upper surface.*—RHS 137B.

*Lower surface.*—Same as upper surface.

*Length.*—0.4-0.5 cm.

*Width.*—Most less than 0.1 cm.

*Shape.*—Lanceolate.

*Apex shape.*—Acute.

*Based.*—Fused.

*Margins.*—Entire; papery and translucent.

*Texture, upper surface.*—Smooth and shiny.

*Lower surface.*—Bifid T-shaped hairs.

Reproductive organs:

*Gynoecium.*—Found on both florets.

*Pistil quantity.*—1.

*Length.*—0.4 cm.

*Style color.*—RHS 1B with RHS 1C basally.

*Style length.*—0.3 cm.

*Stigma color.*—RHS 6A.

*Stigma shape.*—Biparted.

*Ovary color.*—Closest to RHS 157C.

*Androecium.*—Found on only disc florets.

*Stamen quantity.*—Approximately 4-5.

*Color of filaments.*—RHS 155C.

*Length filaments.*—0.1 cm.

*Anther color.*—RHS 15A.

*Anther length.*—0.1 cm.

*Anther shape.*—Ligulate.

*Color of pollen.*—RHS 15C.

*Pollen amount.*—Moderate.

*Fertility/seed set.*—Has not been observed on this hybrid.

Disease/pest resistance: 'Yolindsay' appears to be a little less susceptible to Fusarium.

What is claimed is:

1. A new and distinct variety of *Chrysanthemum* plant named 'Yolindsay,' substantially as illustrated and described herein.

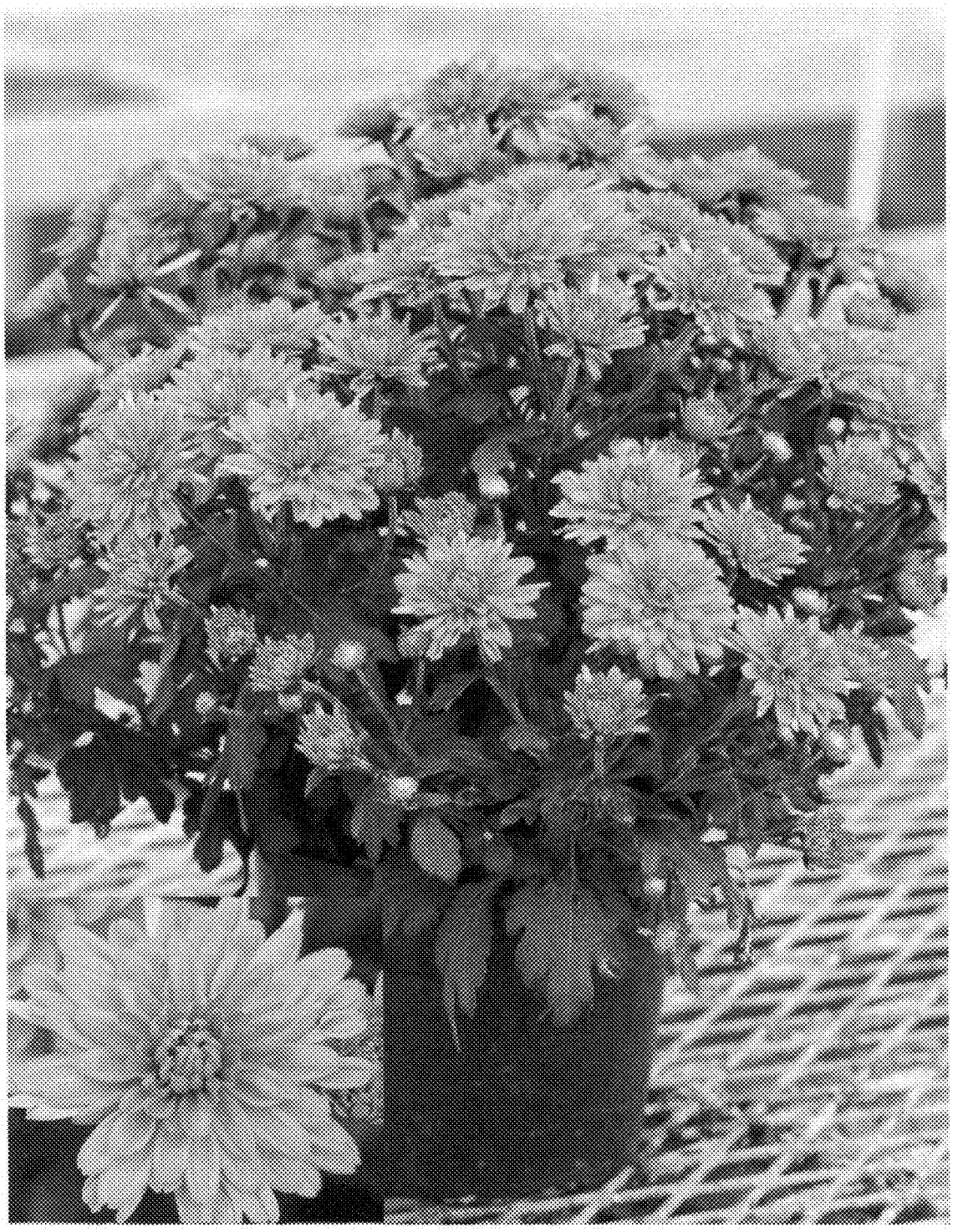

* * * * *